United States Patent [19]

Miles et al.

[11] Patent Number: 5,470,824
[45] Date of Patent: Nov. 28, 1995

[54] METHOD TO TREAT KAPOSI'S SARCOMA

[75] Inventors: Steven A. Miles, Sherman Oaks; Ronald H. Stevens, Marina Del Rey; Otoniel M. Martinez, Valencia, all of Calif.; Tadamitsu Kishimoto, Osaka, Japan; David J. Klashman, Sherman Oaks, Calif.

[73] Assignee: The Regents of the University of California, Oakland, Calif.

[21] Appl. No.: 707,863

[22] Filed: May 31, 1991

[51] Int. Cl.$^6$ .................................................. A61K 37/00
[52] U.S. Cl. .................................. 514/2; 514/44; 530/351
[58] Field of Search ........................... 514/44, 2; 536/27; 530/351; 435/240.2

[56] References Cited

PUBLICATIONS

Rezai et al., J. Cell. Biochem., Suppl. 14D: 176, abstract No. L538 (1990).
Rothenberg et al., J.N.C.I. 81 (20): 1539–1544 (1989).
Ziegler et al., *The Lancet* (Sep. 15, 1984) p. 641.
Maione et al., *Science* (1990) 247:77–79.
Sharpe et al. *JNCI* (1990) 82:848–853.
Brieva et al., *Cellular Immunology* (1990) 130:303–310.
Nakajima et al., *J. Immunol.* (1989) 142:531–536.
Breen et al., *J. Immunology* (1990) 144:480–484.
Miles et al., *Proc. Natl. Acad. Sci.* (1990) 87:4068–4072.

*Primary Examiner*—Jasemine C. Chambers
*Attorney, Agent, or Firm*—Morrison & Foerster

[57] ABSTRACT

Substances or agents which diminish the level of IL-6 or its activity in Kaposi's sarcoma-derived cells are useful agents in the treatment of Kaposi's sarcoma. In particular, substances which inhibit the expression of the gene encoding IL-6 or its receptor, or which interfere with the activity of these substances, are useful in the treatment of this condition. In particular, antibodies immunoreactive with these proteins, oligomers which interfere with the production of these materials, or substances which interfere with the activity of other proteins, DNAs or RNAs that regulate the production and activity of IL-6 are thus useful.

1 Claim, No Drawings

METHOD TO TREAT KAPOSI'S SARCOMA

This work was supported in part by grants from the State of California under the direction of the University-Wide Task Force on AIDS (R87LA039, R88LA078, R90LA121, R86LA012 and 89C-CC86LA), and by the National Institutes of Health (AI24691). The government has certain rights in this invention.

TECHNICAL FIELD

The invention relates to treatment protocols and formulations useful in controlling the course of Kaposi's sarcoma. More specifically, it concerns the use of materials which interfere with the effect of IL-6 to treat this condition.

BACKGROUND ART

Kaposi's sarcoma is a form of malignancy which has particular significance as an opportunistic condition suffered by HIV-infected individuals. It is also seen in individuals who are immunosuppressed for other reasons, such as in transplant recipients.

The nature of the pathology and the origin of the involved cells in Kaposi's sarcoma is not completely understood. It is, however, believed that this is a multi-focal vascular lesion. The frequent association with clinical states characterized by alterations in immune function have led to the postulation that endothelial cells are the cells of origin, but the tumor cells do not have all the immunohistochemical characteristics of vascular endothelia. It has therefore been postulated that the origin is a mesenchymal cell, possibly a lymphatic endothelial cell. Kaposi's sarcoma-derived cell lines are, however, available for study.

A number of treatments have been proposed for Kaposi's sarcoma, including the administration of isotretinoin (13-cis-retinoic acid), a vitamin A analog which is thought to be effective because of its known potentiation of the T-cell immune response and inhibition of virus induction (Ziegler, J., et al. *The Lancet*, Sep. 15, 1984:641). Application has been made for patent coverage of methods to treat Kaposi's sarcoma using the oxide forms of retinene such as cis or trans retinol, retinal, or retonic acid, in combination with an oxidized oil by Dietlin, F., et al., French application no. 2645747, published 19 Oct. 1990. Platelet factor 4 (PF4) and its related peptides have been proposed as a treatment on the basis of the ability of the recombinantly produced factor to inhibit blood vessel proliferation in the chicken chorioallantoic membrane (Maione, T. E., et al. *Science* (1990) 247:77–79; Sharpe, R. J., et al. *J N C I* (1990) 82:848–852).

IL-6 is a cytokine which is known to exhibit a number of functions, including regulation of the differentiation of activated and mature B-cell stages. This cytokine also regulates growth and immunoglobulin secretion by Epstein Barr virus transformed B-cell lines and seems to be essential for mitogen-stimulated B lymphocytes to become immunoglobulin-secreting cells. Brieva, J. A., et al. *Cellular Immunol* (1990) 130:303–310 showed that absent IL-6, most lymphoblastoid B-cells failed to mature to the level of secreting antibody. In addition, it is known that HIV infection elevates the levels of IL-6 in human subjects (Nakajima, K., et al. *J Immunol* (1989) 142:531–536; Breen, E. C., et al., *J Immunol* (1990) 144:480–484).

It has now been found that IL-6 appears to be an autocrine growth factor for AIDS-derived Kaposi sarcoma cells (AIDS-KS cells). This work was published by Miles, S. A., et al., *Proc Natl Acad Sci USA* (1990) 87:4068–4072 which was mailed to subscribers 31 May 1990, and is incorporated herein by reference in its entirety. By virtue of this discovery, the design of agents for the control or treatment of Kaposi's sarcoma that interfere with the action of IL-6 on these cells has been made possible.

DISCLOSURE OF THE INVENTION

The invention provides formulations and treatment protocols for the management of Kaposi's sarcoma. The compositions include active ingredients that are inhibitors of IL-6 or its receptor, that decrease the levels of IL-6 or its receptor, that bind directly to IL-6 or its receptor, or which otherwise interfere with IL-6 activity in Kaposi's sarcoma-involved cells.

Thus, in one aspect, the invention is directed to methods and compositions for the treatment of Kaposi's sarcoma using substances which interfere with IL-6 activity or levels. These substances include binders for IL-6, IL-6 receptor or HIV-tat (which enhances IL-6 activity), substances which interfere directly with the production of IL-6 or IL-6 receptor or the HIV-tat gene product, such as sequence-specific oligonucleotides, or oligonucleotides that react with the binding site for the IL-6 nuclear factor, or, in general, materials which interfere with IL-6 activity such as IL-4.

MODES OF CARRYING OUT THE INVENTION

The seminal observation that IL-6 is an autocrine factor for AIDS-derived Kaposi's sarcoma cells is set forth in detail in Miles, S. A., et al., *Proc Natl Acad Sci USA* (1990) 87:4068–4072, referenced above and incorporated herein by reference. Briefly, cell lines derived from Kaposi's sarcoma lesions of patients with AIDS, designated N521J and EKS3 were shown to secrete large amounts of immunoreactive and biologically active IL-6. Both IL-6 and IL-6 receptor RNA were demonstrated to be present in the cells by slot-blot hybridization analysis and the IL-6 receptor was shown to be functional since exposure of these cells to human recombinant IL-6 at more than 10 units/ml resulted in enhanced labeled thymidine incorporation. Furthermore, the IL-6 antisense oligonucleotide which was a 15 mer specific for a sequence in exon II of the IL-6 gene (as published by Yasukawa, K., et al., *Embo J* (1987) 6:2939), was able to decrease cellular proliferation in AIDS-KS cell lines at optimal concentrations of 15–20 μM. This inhibition of proliferation could be reversed by adding recombinant IL-6. The levels of IL-6 and IL-6 receptor RNA in Kaposi's sarcoma-involved cells were shown to be higher than in cells from uninvolved skin. It was also shown that IL-6 secretion was inhibited by the antisense oligonucleotide.

As IL-6 thus appears to be an autocrine factor necessary for the proliferation of Kaposi's sarcoma cells, substances which interfere directly with the activity of IL-6 or its receptor are useful in the control of the Kaposi's sarcoma condition. In addition, materials which interfere with the production of either or both IL-6 or IL-6 receptor are also thus useful. Among such substances are antibodies specifically immunoreactive with IL-6 or IL-6 receptor, including monoclonal forms thereof or immunologically reactive fragments thereof, other cytokines which reduce the production of IL-6, such as IL-4, antisense oligomers that interfere with the production of IL-6 or IL-6 receptor, and substances which react with and diminish the activity of materials known to enhance the production or activity of IL-6 or its receptor, such as the gene product of HIV-tat or IL-6 nuclear factor.

Antibodies useful in the invention methods can be produced using conventional immunization protocols and harvest of the polyclonal antisera, or immortalization of the antibody-producing cells and screening with the immunogen to provide sources for monoclonal preparations immunoreactive with these targets. Whole antibodies can be used as the active ingredient in the compositions of the invention or, alternatively, immunologically reactive fragments thereof such as the Fab, Fab', or F(ab)'$_2$ fragments can be used. In addition, recombinantly-produced antibodies or portions thereof can also be employed with the flexibility that this permits in design of specifically-reactive antibodies.

In addition, materials which interfere with the production of IL-6, IL-6 receptor or HIV-tat can be used. These materials may be, for example, antisense oligonucleotides or other related oligos directed to these materials. Any region of the coding sequence can be targeted; for example, as set forth in the PNAS paper referred to above, the oligomer TCC-TGG-GGG-TAC-TGG (SEQ ID NO:1) derived from exon II of the IL-6 gene or the sequence CCA-GTA-CCC-CCA-GGA (SEQ ID NO:2) can be used to inhibit IL-6 expression. With respect to the IL-6 receptor, it appears that the sense strand sequences are more effective than antisense sequences in effecting inhibition. However, the ability of the sense strands to inhibit the synthesis of the receptor is clearly sequence-specific. Thus, the oligomeric sequences CCT-GCG-CAG-GAG-GTG (SEQ ID NO:3) or CTG-GCC-CCA-CCA-AGG-CGC-TGC (SEQ ID NO:4) are useful for inhibition of the synthesis of IL-6 receptor protein. The corresponding antisense sequences do not appear to be effective.

The ability of oligonucleotides containing sequences related to those encoding IL-6 receptor or IL-6 can be assessed using assay methods for the production of IL-6 or its receptor as set forth in the "Assay Methods" section below. Thus, it is a simple matter to determine whether a sense sequence, antisense sequence, or modification thereof is thus useful.

In an alternate approach, inhibitory sequences encoding the binding site for IL-6 nuclear factor may also be employed. IL-6 nuclear factor is a protein induced by certain other cytokines that, in turn, induces the production of IL-6. Thus, duplex DNA which reacts with the binding site of IL-6 nuclear factor effectively floods the system and may prevent the binding of nuclear factor to the DNA target. This may result in IL-6 inhibition. Duplexes of the sequence AGA-TTG-TGC-AAT-GT (SEQ ID NO:5) and its complement are effective in suppressing the induction of IL-6 by IL-6 nuclear factor.

In all the foregoing, the oligonucleotides or oligomers may be employed as underivatized phosphodiesters in in vitro assays, but should be made nuclease-resistant for administration in vivo. Thus, oligomers with modified linkages, derivatized forms thereof, or other conventional modifications known in the art are also included within the scope of the oligomers employed in the invention. These modifications include, but are not limited to, substitution for the phosphodiester linkage of phosphorothioate, phorphorodithioate, or methylphosphonate linkages, or other isosteric substitutions, derivatization of the sugars, especially at the 5' or 3' termini with groups which modify the oligonucleotide or label it, and use of substitute bases for A,T,C or G to enhance the binding of the oligomer to its target.

An additional set of candidate substances for active ingredients in the compositions and methods of the invention includes cytokines which regulate the production of IL-6. As shown hereinbelow, the cytokine IL-4 inhibits the production of IL-6, as do TGF-β and γ-interferon at certain concentrations.

An additional illustrative approach to regulating the activity of IL-6 in Kaposi's sarcoma cells takes advantage of controlling the mitogenic effect of the transactivating protein of HIV, HIV-tat, on Kaposi's sarcoma-derived cells (Ensoli, B., et al., *Nature* (1990) 345:84–86). The effect of HIV-tat on the growth of Kaposi's sarcoma-derived cells or lesions has been shown in the foregoing paper and confirmed by Vogel, J., et al., *Nature* (1988) 335:606–611. The effect of HIV-tat has been shown to include the enhancement of production of IL-6 as demonstrated hereinbelow.

Still another illustrative approach grounded in regulating a substance known to modulate IL-6 induction or activity comprises direct inhibition of, or inhibition of the production of, oncostatin-M, which is known to induce the production of IL-6. This protein, which is produced by Kaposi's sarcoma cells, can be itself regulated, for example, using the antisense inhibitor GCT-GCC-TAT-AGC-CGC (SEQ ID NO:6), which targets the coding sequence for oncostatin-M. Alternative strategies to regulate the production and activity of oncostatin-M could also be used.

All of the foregoing approaches have as their effect the control of the production or activity of IL-6 in the Kaposi's sarcoma cell targets.

Assay Methods

Any candidate as an agent for intervention in the progress of Kaposi's sarcoma can be evaluated and identified as a successful active agent in this respect by examining the effect of this candidate anti-Kaposi's sarcoma agent on the level or function of IL-6 in suitable cells or cell lines in vitro. Assessment of the effect of candidate agents on IL-6 levels or function can be approached in a number of ways.

First, the level of IL-6 production in subject cells or cell lines can be measured directly by assessing the amounts of IL-6 itself or the level of mRNA encoding IL-6 in the presence and absence of the candidate agent. For example, described in detail herein is an ELISA assay for IL-6 protein. Also described is a slot blot assay for IL-6 mRNA. Other methods of quantification include PCR RNA hybridization assays.

Second, the influence of a candidate agent on the function of IL-6 can be measured by using, as a substrate, cells which are known to be responders to IL-6 activity and assessing the effect of the candidate agent on the response of these cells to added IL-6. For example, described hereinbelow is an assay which utilizes thymidine uptake as a measure of proliferation in an IL-6 dependent cell line. The assay is conducted in the presence and absence of the candidate agent, and agents that result in lowered cell proliferation are considered successful candidates for evaluation and use as inhibitors of IL-6 function.

In another approach, the effect of candidate agents on substances which are known to mediate or enhance the effect of IL-6 can be used as an indirect indicator of effect on IL-6 function. Thus, the effect of the candidate agent on the production or function of the IL-6 receptor or on the production or function of the gene product of HIV-tat which is known to enhance the function of IL-6 can be used. The levels of production of these substances (IL-6 receptor and HIV-tat gene product) can be measured in a manner analogous to that for the production of IL-6—i.e., by direct measurement of the protein product through, for example, an ELISA assay or by measurement of the amounts of mRNA encoding these products present in the cells in the presence and absence of the candidate reagent.

Some exemplary procedures for assessing the effect of candidate anti-Kaposi's sarcoma agents follow.

One assay for the capacity of candidate anti-Kaposi's sarcoma agents to effect decreased IL-6 production in vitro is conducted by quantifying IL-6 using an IL-6-specific ELISA. Flat-bottom 96-well plates are coated with a murine monoclonal antibody against human IL-6 ($\alpha$-BSF2-166) as described by Matsuda, T., et al., *Eur J Immunol* (1988) 18:9151–9156. The wells are exposed to cell supernatants of unknown IL-6 concentration or to standard concentrations of IL-6 diluted in medium, washed, and incubated with rabbit anti-IL-6 serum (Genzyme). The wells are again washed, incubated with goat anti-rabbit serum coupled to horseradish peroxidase and developed with a standard substrate (0-phenylenediamene dihydrochloride). IL-6 levels are then determined by comparison of experimental absorbance with a standard curve obtained with known quantities of IL-6 in the same assay.

The effects of increased or decreased IL-6 production can also be measured indirectly using a cell proliferation bioassay based on the proliferation and incorporation of labeled thymidine in the IL-6 dependent murine hybridoma MH60 BSF2 line described by Nakajima, K., *J Immunol* (1989) 142:531–536, and by Matsuda, T., et al., (supra). The IL-6 activities are expressed as equivalent amounts of human recombinant IL-6 units/ml required for the same biological activity.

A slot-blot hybridization assay for mRNA encoding IL-6 or IL-6 receptor in cell cultures which normally, or which are stimulated to, produce IL-6 is conducted by extracting total RNA with guanidine isothiocyanate and ultracentrifuging in cesium chloride as described by Maniatis, T., et al., "Molecular Cloning: A Laboratory Manual" (1982) Cold Spring Harbor Laboratories, Cold Spring Harbor, N.Y. Total RNA in amounts ranging from 2.5–0.31 μg is blotted onto a nylon membrane (GeneScreen Plus NEN) and the membrane is baked, prehybridized and then hybridized at 42° C. for 24 hours with a suitable probe. The hybridization solution is 50% (v/v) formamide, 1% SDS, 1M NaCl, 10% dextran sulfate and denatured salmon sperm DNA at 150 μg/ml with a labeled probe. The probe comprises $^{32}$P-labeled 440 bp TaqI-BanII fragment of IL-6 cDNA as described by Hirano, T., et al. Nature (1986) 324:73–76 or a $^{32}$P-labeled 1700 bp XhoI fragment of IL-6 are receptor cDNA as described in Yamasaki, K., et al. *Science* (1988) 241:825–828 or $^{32}$P-labeled β-actin cDNA.

Alternatively, the effect of agents on Kaposi's sarcoma directly can be measured by a cell proliferation assay on Kaposi's sarcoma-involved cells. Kaposi's sarcoma-involved cells harvested by digestion with trypsin/EDTA are plated in 96-well plates and allowed to grow for 24 hr in the presence of 20% HTLV-2 conditioned medium (supernatant of passage 107 of MOT cells with 10% fetal bovine serum in IMDM). To reduce background stimulation from growth medium, the medium is removed and replaced with serum-free medium (IMDM with ITS+ (Collaborative Research) and ECGS at 30 μg/ml, heparin at 10 USP units/ml and human fibronectin). After a 6 hr washout period, the medium is removed and replaced with serum-free medium containing recombinant IL-6 (0–30 U/ml for 24 hr at 37° C. and 5% $CO_2$). Labeled thymidine is added 1 μCi per well for 18 hr and the cells are released with trypsin/EDTA and harvested into glass filter strips. Radioactivities are measured in a liquid scintillation fluor.

Administration and Use

The substances used as active ingredients in the compositions of the invention are formulated in conventional ways such as those set forth in *Remington's Pharmaceutical Sciences*, Mack Publishing Co., Easton, Pa., latest edition. Generally, the compositions are administered systemically, preferably by injection. Formulation for injection generally includes use of excipients such as Hank's solution, Ringer's solution, or other physiological buffers compatible with the blood stream. Other forms of systemic administration include transdermal and transmucosal administration using excipients which ease the transfer of substances across membranes or epidermis. Such excipients include detergents, bile salts, fusidic acid derivatives and the like or combinations thereof. In addition, under proper circumstances, oral administration may also be used.

In general, the dosage levels required depend on the potency of the anti-Kaposi's sarcoma agent, the severity of the condition, the mode of administration, the nature of the formulation, and the judgment of the attending physician. Optimization of dosage levels is obtained using routine optimization procedures starting from the level of potency determined for the effect in lowering IL-6 function in in vitro tests as described above. For example, from the in vitro results with respect to IL-4, it is estimated that amounts on the order of 1 mg/kg/day of this cytokine is an approximately appropriate dose.

The anti-IL-6 agents of the invention which are oligomers or modified forms thereof are best administered by injection parenterally.

The antibody or antibody fragment active ingredients are formulated in a manner conventional for such medicaments and employed at a dosage level effective to bind the IL-6, IL-6 receptor, or HIV-tat targets.

Subjects who harbor the Kaposi's sarcoma condition exhibit a multitude of skin lesions which can be treated locally in some instances in addition to the benefit derived from systemic treatment. Thus, the anti-IL-6 agents of the invention can be administered topically or by injection directly to the desired site of activity. Indeed, a convenient method to assess the effectiveness of a candidate agent is to administer the candidate only to selected lesions and to inject the alternate lesions with control. Under some circumstances, the agents of the invention can be used as a substitute for radiation therapy or surgery which might otherwise be used to remove or reduce the localized manifestation of the condition. However, it is currently believed that concomitant systemic treatment is also desirable, as the distribution of Kaposi's sarcoma involved cells is not believed to be entirely localized in the visible lesions.

The following examples are intended to illustrate but not to limit the invention.

EXAMPLE 1

Effect of IL-4 and Other Cytokines on IL-6 Production and Function

AIDS-KS-derived cell lines NU1PV, CG1, F1RR and DM1 were isolated and characterized from pleural effusions of four different patients with AIDS-related KS as described by O'Brien, R. F., et al., *Chest* (1989) 440–446. Briefly, pleural fluid was obtained by thoracentesis and a cell pellet was isolated by centrifuging at 800 g for 15 min. Cell pellets from multiple tubes were combined, washed with Iscove's modified Dulbecco's medium (IMDM), and resuspended at $4 \times 10^6$ cells/ml in growth medium (IMDM containing 20% FBS, 30 μg/ml endothelial growth supplement (Sigma), 1% penn/strep with Fungizone (Gibco), 100 USP units/ml sodium heparin (Sigma), supplemental L-glutamine and 10% HTLV-2 conditioned media (MO cell lines provided by Dr. David Golde, UCLA)). Cells were added to flasks previously coated and allowed to dry with 0.5% gelatin. Twenty-four hours later the nonadherent cell fraction was removed and the flasks were washed with phosphate-buffered saline (PBS). Fresh growth medium was added and the cells were incubated at 37° C. in a humidified atmosphere with 5% $CO_2$. Confluent monolayers were obtained at 3–7 days. The monolayers were harvested with Trypsin-EDTA solution (1×, Irvine Scientific) and serially passaged. Cell lines for subcloning were obtained by limiting dilution culture of confluent monolayers on 96-well plates previously coated with 0.5% gelatin. After approximately 3–5 weeks, single-cell isolates were obtained.

The cell lines were characterized by immunohistochemical staining, including staining for Factor VIII-related antigen (Sigma), Ulex europeas-1 lectin antigen (Sigma), angiotensin-converting enzyme, and Type IV collagen. The cell lines stained variably for Factor VIII antigen, uniformly with strong reactivity for Ulex europeas-1 lectin antigen, and variably for Type IV collagen. Only rare early-passage cells were positive for angiotensin-converting enzyme antigen.

The cell lines were maintained in subconfluent continuous monolayer cultures utilizing growth media in gelatinized flasks. Proliferation was checked periodically using labeled thymidine incorporation, and cell lines were maintained in culture for up to 30 passages. After this number of passages, cell lines had marked decrease in proliferation and were no longer used in the assays.

For the assay, subconfluent monolayers of AIDS-KS-derived cells were washed twice with phosphate-buffered saline. The monolayers were trypsin/EDTA harvested, cells were counted, viability determined by trypan blue exclusion, and the cells were replated at $5 \times 10^4$ cells/200 µl in growth media in 96-well plates previously coated with 0.5% gelatin. Twenty-four hours after plating, the supernatant medium was removed and serum-free IMDM containing 100 USP units/ml sodium heparin, 1% penn/strep with fungizone, and ITS+ (Collaborative Research, Cambridge, Mass.) was added with various cytokines at the following concentrations:

| | |
|---|---|
| TNF-α | 8, 40, 200, 1000 u/ml |
| IL-1β | 8, 40, 200, 1000 u/ml |
| Oncostatin-M | 2, 10, 50, 250 ng/ml |
| IL-4 | 20, 100, 500, 2500 ng/ml |
| PF-4 | 10, 25, 50, 125 µg/ml |
| TGF-β | 0.4, 2, 10, 50 ng/ml |
| γ-Interferon | 8, 40, 200, 1000 u/ml |
| SCF | 10, 100, 1000 ng/ml |

(To prevent inhibition of PF4 by heparin, studies of recombinant platelet factor 4 (PF4) and the controls for that experiment were preformed in heparin free, serum free media 24 hours after plating in growth media.)

After a 6 hour wash-out period, the medium was removed and replaced with serum-free media containing the cytokines for 24 hr at 37° C. in a 5% $CO_2$ atmosphere. [$^3$H] Thymidine was added at 1 µCi per well (1 µCi=37 kBq) for 18 hr.

Supernatant media was removed for IL-6 ELISA assays. The cells were released with trypsin/EDTA harvested onto glass wool filters, and radioactivities were measured in a scintillation fluor. Each assay was done in quadruplicate and the assays were repeated on all four of the cell lines.

For the Interleukin-6 ELISA assay, flat bottom 96 well plates were coated with a murine monoclonal antibody against human IL-6 (α-BSF2-166), exposed to supernatants of unknown concentration or standard concentration of hrIL-6 diluted in medium, washed, incubated with rabbit anti-IL-6 serum (AmGen), washed, incubated with goat anti-rabbit serum coupled to horseradish peroxidase and developed with a standard substrate (o-phenylenediamine dihydrochloride, OPD). IL-6 levels were determined by comparison of experimental OD with a standard curve obtained with known quantities of hrIL-6 obtained in the same assay.

Biologic activity of secreted IL-6 in the supernatants was measured using a cell proliferation bioassay. This assay is based on the proliferation and incorporation of $^3$H-thymidine in the IL-6-dependent murine hybridoma MH.BSF-2 line. Growth of this cell line is absolutely dependent on IL-6. The IL-6 activities in the supernatants are expressed as equivalent amounts of hrIL-6 (units/ml required for the same biological activity.

Three patterns of response in AIDS-KS cell proliferation and IL-6 production were observed with these cytokines. TNF-α, IL-1β, and Oncostatin-M all increased AIDS-KS cell line proliferation of multiple cell isolates in a concentration dependent manner. The half-maximal stimulation concentrations were <8 units/ml for TNF-α, 8 ng/ml for IL-1β and 2 ng/ml for Oncostatin-M. In each case, the increase in proliferation was mirrored by increases in IL-6 production and secretion into the supernatant media as detected by an IL-6 specific ELISA.

Unlike the increase in AIDS-KS cell proliferation and IL-6 secretion induced by exposure to TNF-α, IL-1β, and Oncostatin-M, a decrease in proliferation and IL-6 production was seen with interleukin-4 and the endothelial cell inhibitor platelet factor-4 (PF4). Interleukin-4 inhibited growth of Kaposi sarcoma cells by greater than 50% in culture at concentrations less than 20 ng/ml. Near complete inhibition of IL-6 secretion was seen at similar concentrations but increases in IL-6 secretion without corresponding increases in proliferation were seen at the highest concentrations examined (2500 ng/ml). Because of this "rebound" in IL-6 secretion by IL-4 at 2500 ng/ml, IL-6 antisense oligonucleotides significantly decreased this IL-6 secretion resulting in further suppression of AIDS-KS cell growth. Using the endothelial cell inhibitor platelet factor-4 in heparin free media, a dose dependent inhibition of AIDS-KS cell proliferation was seen. Accompanying this inhibition of proliferation was a decrease in the secretion of IL-6 into the supernatant media. While the antisense IL-6 oligonucleotide did decrease the AIDS-KS cell line proliferation further, this effect was minimal suggesting that, at this concentration of PF4, there was already significant inhibition of IL-6.

Finally, evaluation of the effects of transforming growth factor-beta$_1$ (TGF-β$_1$) and gamma interferon revealed a more complex, biphasic response. TGF-β$_1$ increased proliferation at the lowest concentrations but inhibited the growth of AIDS-KS cell lines at higher concentrations. In contrast, gamma interferon inhibited AIDS-KS cell lines at low concentrations but increased proliferation at higher concentrations. However, even in the more complex pattern of response induced by these cytokines, increases or decreases in cell growth were accompanied by simultaneous increases or decreases in the secretion of IL-6 into the media. As seen with the other cytokines, antisense IL-6 oligonucleotides reversed the stimulation observed with gamma interferon and further augmented the inhibition of proliferation seen with TGF-β$_1$.

One additional cytokine, human stem cell factor (SCF), was evaluated. No effects on AIDS-KS cell proliferation was seen in any of the 4 cell lines examined. There were no alterations in IL-6 secretion with exposure to SCF and the IL-6 antisense oligonucleotides inhibited the proliferation of the AIDS-KS cell lines in the same manner as seen with the control media.

| Half-Maximal Concentration of Cytokines for their Effects on AIDS-KS Cell Lines | | |
|---|---|---|
| Cytokine | Effect | Mean Half-Maximal Concentration |
| Tumor Necrosis Factor alpha (TNF-α) | Positive | <8 u/ml |
| Interleukin-1 beta (IL-1β) | Positive | 8 u/ml |
| Oncostatin-M | Positive | 2 ng/ml |
| Interleukin-4 (IL-4) | Negative | <20 ng/ml |
| Platelet Factor-4 (PF4) | Negative | 15 μg/ml |
| Tranforming Growth Factor beta$_1$ (TGF-β$_1$) | Biphasic | Not Applicable |
| Gamma Interferon | Biphasic | Not Applicable |
| Human Stem Cell Factor (SCF) | None | No effect up to 1000 ng/ml |

Overall, for the four cell lines and eight cytokines examined, there was an excellent correlation between the magnitude of stimulation of IL-6 secretion and proliferation of AIDS-KS cell lines. There was also an excellent correlation between the magnitude of inhibition by the antisense IL-6 oligonucleotide and the magnitude of alteration in cell proliferation by the cytokine (data not shown).

Thus, as shown in this example, IL-4 and PF-4 are able to decrease the effect of IL-6 and are thus candidate agents. TGF-β and γ-interferon, at appropriate concentrations, are also able to do so. On the other hand, TNF-α, IL-1β, oncostatin-M all induce IL-6 formation or effect, and therefore agents which interfere with their function or levels will also be successful candidates for evaluation and use in control of Kaposi's sarcoma.

EXAMPLE 2

Effect of HIV-tat on IL-6 production and function

Recombinantly produced HIV-tat, but not mutant HIV-tat, was shown to increase labeled thymidine incorporation in a dose-dependent manner in AIDS-KS-derived cells. The cells were prepared and characterized as described in Example 1. Expression vectors for HIV-tat and mutated forms thereof have already been described by Garcia, J. A., et al., *Embo J* (1988) 10:3143–3147. Subconfluent monolayers of AIDS-KS-derived cells were washed twice with PBS and exposed to calcium phosphate precipitation using HIV-tat and a mutant HIV-tat expression construct at concentrations up to 10 μg/ml, and the cells were allowed to proliferate for an additional 24 hours. Forty-eight hours after transfection, the monolayers were trypsin-EDTA harvested, cells were counted, viability determined by trypan blue exclusion, and the cells were replated at $5\times10^4/200$ μl in growth medium in 96-well plates previously coated with 0.5% gelatin. Twenty-four hours after plating (72 hours after transfection) the supernatant media were removed and serum-free IMDM containing 100 USP units/ml sodium heparin, 1% penn/strep with fungizone, and ITS+ were added. One μCi/ml of labeled tritiated thymidine was added to each well, and the cells were incubated at 37° C. in a humidified incubator with 5% $CO_2$ for 24 hours. The supernatant media were then subjected to IL-6 ELISA assays as described in Example 1. The cells themselves were trypsin-EDTA harvested as described by Miles, S. A., et al., *Proc Natl Acad Sci USA* (1990) 87:4068–4072, on glass wool filters and counted in scintillation fluid. Each assay was done in quadruplicate, and the assays were repeated on at least three of the four cell lines.

The results showed significant increases in thymidine incorporation with the HIV-tat construct but not the mutated HIV-tat vector, and these increases were associated with corresponding significant increases in secreted IL-6 as detected by IL-6 ELISA. Increases in proliferation of NU1PV, F1RR, and CG1 cell lines were dose-dependent up to 6 μg/ml of transfected vector and corresponded to increases in IL-6 levels.

We claim:

1. A method to intervene in the progress of Kaposi's sarcoma, which method comprises administering to a subject in need of such intervention an amount of IL-4 effective to decrease IL-6 function in Kaposi's sarcoma-involved cells.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TCCTGGGGGT ACTGG                      1 5

( 2 ) INFORMATION FOR SEQ ID NO:2:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:2:

CCAGTACCCC CAGGA                           15

( 2 ) INFORMATION FOR SEQ ID NO:3:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

CCTGCGCAGG AGGTG                            15

( 2 ) INFORMATION FOR SEQ ID NO:4:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

CTGGCCCCAC CAAGGCGCTG C                     21

( 2 ) INFORMATION FOR SEQ ID NO:5:

( i ) SEQUENCE CHARACTERISTICS:
    ( A ) LENGTH: 14 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:5:

AGATTGTGCA ATGT                              14

( 2 ) INFORMATION FOR SEQ ID NO:6:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

GCTGCCTATA GCCGC                            15